United States Patent [19]

Degnan

[11] Patent Number: 5,269,681
[45] Date of Patent: Dec. 14, 1993

[54] INTEGRATED LIGATURE AND ORTHODONTIC BRACKET

[76] Inventor: Edward V. Degnan, 1850 Ellis St. - 219, Dubuque, Iowa 52001

[21] Appl. No.: 883,529

[22] Filed: May 15, 1992

[51] Int. Cl.$^5$ ............................................. A61C 3/00
[52] U.S. Cl. ..................................... 433/11; 433/15
[58] Field of Search .................... 433/8, 9, 10, 11, 12, 433/13, 14, 15, 16, 17, 18, 19, 20, 21, 22, 23, 24

[56] References Cited

U.S. PATENT DOCUMENTS

| | | | |
|---|---|---|---|
| 2,548,864 | 4/1951 | Brusse | 433/11 |
| 3,193,930 | 7/1965 | Bien | 433/11 |
| 3,959,880 | 6/1976 | Andrews | 433/21 |
| 4,149,314 | 4/1979 | Nonnenmann | 433/11 |
| 4,419,078 | 12/1983 | Pletcher | 433/10 |
| 4,492,573 | 1/1985 | Hanson | 433/11 |
| 4,547,153 | 10/1985 | Taylor | 433/11 |
| 4,614,497 | 9/1986 | Kurz | 433/8 |
| 4,655,708 | 4/1987 | Fujita | 433/10 |
| 4,669,980 | 6/1987 | Degnan | 433/8 |
| 4,698,017 | 10/1987 | Hanson | 433/11 |
| 4,712,999 | 12/1987 | Rosenberg | 433/11 |
| 4,725,229 | 2/1988 | Miller | 433/11 |

*Primary Examiner*—John J. Wilson
*Attorney, Agent, or Firm*—James C. Nemmers

[57] ABSTRACT

The invention provides a ligature that has a defining formed shape and is affixed and integrated with the formed shape of the orthodontic bracket. The ligature can be repeatedly opened, closed, locked, or unlocked, in its integrated relation to the bracket. If necessary, the entire integrated ligature can be removed and replaced. Also, the removed ligature can be replaced by a similar ligature having a variance in the defining formed shape thereof. The integrated ligature has properties of, shape memory, elasticity, flexibility, and resistance to fatigue. The bracket has one or more arch wire receiving channels therein. The bracket also has, in addition to its relation to the integrated ligature, retention concavities in the upper and lower sides of the bracket to provide retention areas for auxiliary devices and/or supplemental ligatures. The integrated ligature and orthodontic bracket has a unique mechanical flexation response mechanism providing for continuous used and repeatable, opening, closing, locking and unlocking, of the ligature in its integrated relation to the bracket.

19 Claims, 5 Drawing Sheets

INTEGRATED LIGATURE AND ORTHODONTIC BRACKET

FIELD OF THE INVENTION

The invention pertains to an Orthodontic Ligature and an Orthodontic Bracket, that being integrated, provide the mechanical confinement or relation of orthodontic materials or devices.

BACKGROUND AND PRIOR ART

My U.S. Pat. No. 4,669,980 is hereby disclosed as prior art, with particular reference to the defined formed shape of orthodontic brackets.

The prior art reveals various types of ligatures and many orthodontic brackets. However, the types of ligatures are primarily of two types. The first type provides a ligature that is placed and removed individually and are disposable.

The second type is a ligating means that is incorporated within the function of a bracket, and the ligation occurs when a portion of the bracket is moved into a particular relation with other portions of the bracket, and that movement captures an orthodontic arch wire therein. Both types of the ligature can capture an arch wire therein.

The formed shape and size of an orthodontic bracket is important in orthodontic treatment procedures. All of the brackets are designed to utilize some type of ligation method.

The prior art reveals an evolution of primarily two types of ligatures. The prior art also reveals the evolution of primarily two types of brackets.

Each of the two types of ligatures have influenced the design, shape, and size, of each of the two types of brackets. Each type of ligature and each type of bracket has advantages and disadvantages in using them in orthodontic treatment procedures. The width, height and thickness, of brackets, accommodating the disposable types of ligatures, can have more variations in their size without compromising the use of disposable ligatures. This is due to the various sizes and shapes of disposable ligatures that can be used. Disposable ligatures made of elastic plastic, have decreasing elasticity over time and need frequent replacement. This is a disadvantage, if their use requires continuous elasticity. Another disadvantage is that disposable ligatures produce a tight relation of the bracket to an arch wire, and this can cause a frictional deterrent to certain types of tooth movement. The metal type of disposable ligatures are difficult to place and remove, and do not have elasticity. These two factors also are disadvantages. Disposable metal ligatures can become uncomfortable, if the twisted end thereof becomes dislodged from its intended comfortable position. This is also a disadvantage of their use.

The types of ligatures and brackets that are revealed in the prior art, have both advantages and disadvantages in their use. The bracket design, shape, and size, and the width, height, and thickness are influenced by the ligation mechanism within the bracket. This is particularly evident in the mechanism in the instance of the non-disposable type of ligature that may be permanently incorporated in a bracket. This can produce disadvantages of width, thickness, height, design, shape, or size.

The invention herewith presented incorporates the advantages of the two primary types of ligatures, and the advantages of the two primary types of brackets; into the defining formed shape and size, of the Integrated Ligature and Orthodontic Bracket.

Some of the advantages of the inventions are as follows. The Integrated ligature can be repeatedly locked and unlocked in relation to the bracket, without a need to replace the ligature, or the ligature can be completely removed from the bracket and then replaced if necessary.

The ligature does not lose its elasticity.

The ligature does not need to be completely removed and replaced numerous times during orthodontic treatment, as is often necessary when disposable ligatures are used.

The integrated ligature and bracket remain comfortable throughout treatment because of its small size, shape, and contours.

The ligature can be completely removed and replaced, if desired, however, this would be an exception to the usual method of the use of the integrated ligature.

The size and shape of the bracket is variable without compromising the efficiency, because of the presence of the Horizontal and Vertical channels in one version of the brackets, and because of the shape memory, and resilience, of the integrated ligature. There are no shapes or ingredients of form to cause discomfort.

The Integrated Ligature and Bracket incorporate the advantages of the two primary types of ligatures and the two primary types of brackets. Therefore, the practitioner of orthodontic has a continuous opportunity to choose the advantages he or she prefers to use in treatment procedures.

The presence of a vertical channel in one version of the bracket and also the presence of a horizontal channel in the same bracket, expands the utility and the number of uses, of the Integrated Ligature and Bracket.

BRIEF SUMMARY OF THE INVENTION

The invention is the integration of a ligature with a defining formed shape of an orthodontic bracket, in a new and useful way, to provide the mechanical confinement or relation of orthodontic materials and devices. The ligature is a wire formed of metal having a radius in its diameter to form a circle, and is called a round wire. The ligature progresses without interruption as it relates to, an orthodontic arch wire receiving channel or channels, of the bracket, and an orthodontic ligature receiving channel in each of two sides of the orthodontic bracket.

The integrated ligature can be closed or opened, and locked or unlocked, in its relation to the bracket. The invention incorporates, in an Integrated Ligature and Bracket, the two primary types of ligatures, and the two primary types of brackets revealed in the prior art. The combination of these primary types of ligatures and brackets into an integrated ligature and bracket, substantially increases the usefulness and utility of the ligature and bracket of this invention.

The Invention also provides two versions of an orthodontic bracket. One of the versions has a single orthodontic arch wire receiving channel. The other version has two orthodontic arch wire receiving channels. These two are a horizontal channel and a vertical channel.

EMBODIMENT OF THE INVENTION

Figure 1:
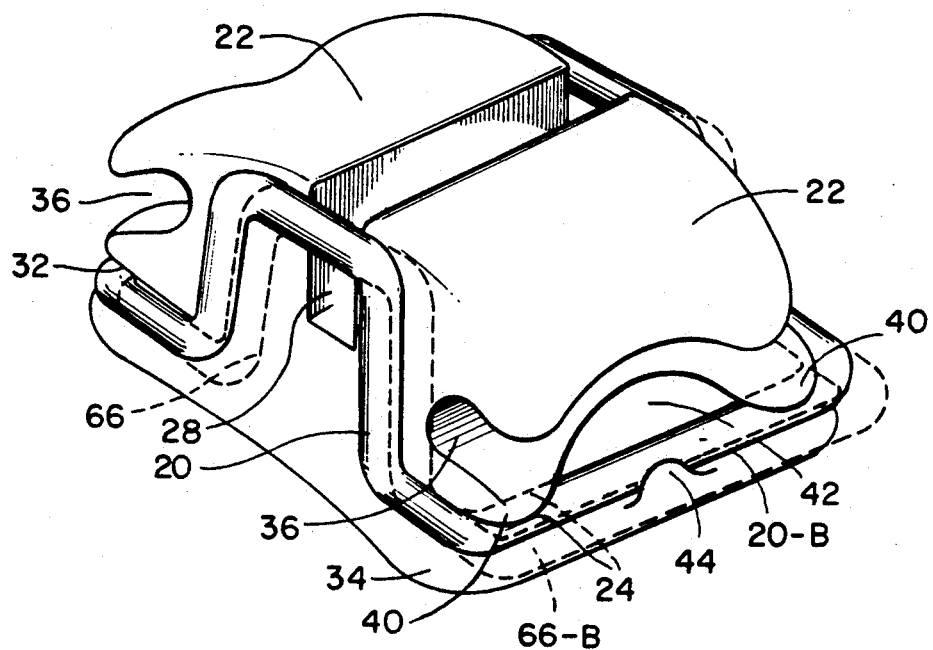
FIG. 1, is an illustration of the Integrated Ligature and Orthodontic Bracket, with the upper side facing the examiner thereof. The illustration incorporates a broken line showing the movement of the ligature during the unlocking of the ligature from a locked position. The illustration depicts the version of the bracket having one arch wire receiving channel in the bracket, called the horizontal channel.

The invention is an Integrated Ligature and Orthodontic Bracket. FIG. 1,2,3,4,5,12. Ligatures and Orthodontic Brackets are commonly used in providing Orthodontic Treatment.

The size of a conventional type small bracket was used for the orientation of the development of this invention.

The development of this invention had, as a size orientation, a bracket that is 4 milimeters in vertical height and 3.8 milimeters in horizontal width. The orientation for the thickness of the bracket was 2.5 milimeters.

These comments and the numerical values are a guide for thought orientation, and are not absolute values, to be applied.

The dimensions of orthodontic brackets, acceptable for the treatment of people, are influenced by the sizes that can be accommodated safely and acceptably. The safety and acceptability is influenced by the function of the dental arches of teeth in relation to each other, and the way they occlude with each other, during the function and apposition of the jaws that contain the dental arches of teeth. These factors place limitations on the acceptable sizes and shapes of orthodontic brackets, that would be commonly useful in providing orthodontic treatment. The size and defining formed shape, of the bracket, is also influenced by the mechanical attributes necessary, to be useful in providing orthodontic treatment.

An orthodontic bracket, FIG. 1(22), in general terms, may be described as small block of metal, that has a defining formed shape, suitable for placement upon the surface of teeth, as a participating device, in providing orthodontic treatment. Ligatures of various types of material and size are used in orthodontic treatment. For thought orientation, the Integrated Ligature FIG. 1(20) used in the development of this invention, was a metal wire ligature having a diameter of 0.014 of an inch. The diameter of the ligature has a specific relation to the ligature receiving channels defined in the formed bracket, FIG. 1(24) and FIG. 2(24). The ligature is continuous in shape, and progresses without interruption, in its defining formed shape, as it relates in an integrated manner with the defining formed shape of the bracket.

Figure 3:
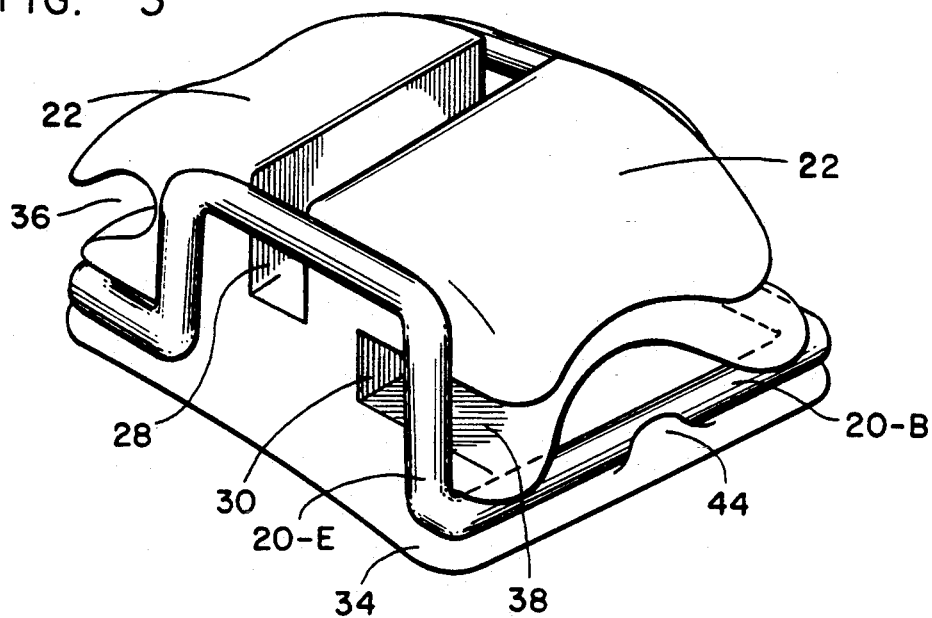
FIG. 3, is an illustration of the Integrated Ligature and Bracket, with the upper side facing the examiner thereof. The illustration depicts the version of the bracket having two arch wire receiving channels. The two channels are, a horizontal channel and a vertical channel.

The two primary components of the invention are: an orthodontic ligature, FIG. 1(20), and orthodontic brackets, FIG. 1(22) and FIG. 3(22).

The ligature has an integrated relation to the defining formed shapes in the orthodontic brackets. The bracket has a design and configuration that makes it suitable for attachment upon an area of the clinical crown of a tooth of a person. The ligature, FIG. 1(20), has a design and configuration that makes it suitable to integrate with the defining formed shape of the orthodontic bracket. The ligature is a metal wire, FIG. 1(20), that progresses without interruption in a relation to the defining formed sides and specific relevant channels of the bracket. The ligature is formed of metal that has physical properties of shape memory to maintain an established shape, and properties of appropriate strengths, resilience, ductility, and resistance to fatigue, to be used for the defining formed shape and function of the integrated ligature of this invention.

The bracket has two kinds of channels formed in the bracket. The first, FIG. 1 (28) is the type formed to receive an orthodontic arch wire. The second, FIG. 1(24), is the type of channel formed to receive and relate to a portion or section of the integrated ligature.

Each bracket has width,, height,, and depth. The bracket is usually placed upon either the facial or lingual surface of the clinical crown of a tooth. The side of the bracket that interfaces with the surface of a tooth is called the base of the bracket, FIG. 1(34). When the bracket has the base attached to the facial surface of a tooth, the side of the bracket opposite to the base is called the facial side of the bracket. When the bracket has the base attached to the lingual surface of a tooth, the side of the bracket opposite to the base is called the lingual side of the bracket.

The side of the bracket that faces toward the anterior mid-line of the dental arch is called the mesial side of the bracket. The side of the bracket that faces away from anterior mid-line of the dental arch is called the distal side of the bracket.

For purposes of orientation and clarity in describing the embodiment of the invention: the side of the bracket facing upward will be called the upper side, when the bracket is placed upon either the facial or lingual surface of a tooth of a person. The side of the bracket facing downward will be referred to as the lower side of the bracket, when the bracket is placed upon either the facial or lingual surface of a tooth of a person.

There are two versions of the bracket presented. They differ from one and the other, by the number of orthodontic arch wire receiving channels present in the respective bracket.

Figure 2:
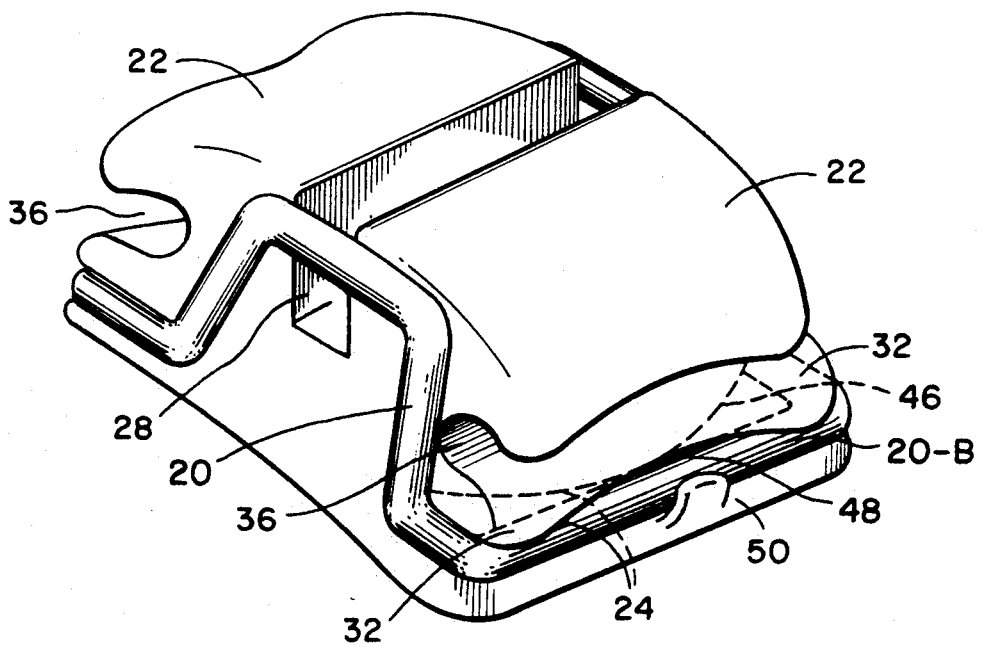
FIG. 2, is an illustration of the Integrated Ligature and Orthodontic Bracket, with the lower side facing downward. The illustration depicts the version of the bracket having one arch wire receiving channel in the bracket, called the horizontal channel.

The first version, FIG. 1(28) and FIG. 2(28), has a channel traversing the facial surface of the bracket in a mesial to distal direction. The open side of the channel faces facially, when the base of the bracket is upon the facial surface of a tooth. This channel is called the horizontal channel, and is suitable to receive an orthodontic arch wire. The second version of the bracket, FIG. 4(30), has a second channel, to receive an orthodontic arch wire. The second channel traverses the upper side of the bracket in a mesial to distal direction. The open side of this second channel faces upward. This channel is called the vertical channel of the bracket, and is suitable to receive an orthodontic arch wire.

The following is a narrative pertaining to the content of the figures of the drawings. The narrative follows the sequence of the numbered figures of the drawings.

FIG. 1, is an illustration of the Integrated Ligature and Orthodontic Bracket,, with the upper side facing the examiner thereof. The illustration incorporates a broken line showing the movement of the ligature during the unlocking of the ligature from its locked position. This illustration depicts the version of the bracket having one arch wire receiving channel in the bracket, called the horizontal channel.

The ligature, FIG. 1(20), can be seen progressing without interruption in relation to the horizontal channel of the bracket, FIG. 1(28), and progressing into the ligature receiving channel, FIG. 1(24), at the upper side of the bracket that faces the examiner thereof, in FIG. 1.

The ligature, FIG. 1(20), is in a closed locked position. The ligature provides a relation at the open side of the channel, FIG. 1(28), that causes closure of the rectangular shaped channel at the channel's open side. A retention cove, FIG. 1(36), traverses the bracket in a mesial to distal direction. This cove provides a retention area for auxiliary devices, and/ or ligatures.

The flange-shaped areas, FIG. 1(40), participate in forming the channel receiving the ligature in the upper side of the bracket, and in the lower side of the bracket.

Figure 7:
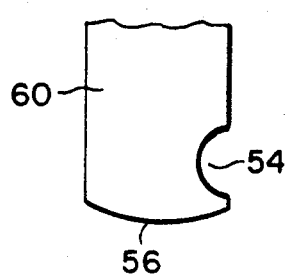
FIG. 7, is an illustration of the end portion of the instrument used to unlock the Integrated Ligature from the upper side of the Bracket. This illustration is a view of the widest side of the instrument.
Figure 8:
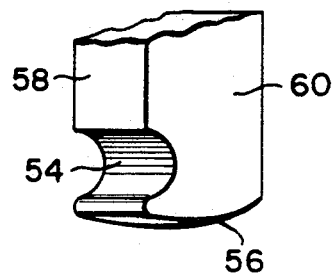
FIG. 8, is an illustration of an oblique view of the instrument shown FIG. 7., This instrument is used to unlock the Integrated Ligature from the upper side of the Bracket.

The concave shaped inlet area between the two flanges, FIG. 1(42),, provides an entrance area and access for the instrument, FIGS. 7, 8, that is used to unlock the ligature from its locked position, where it resides in the ligature receiving channel. The size and shape of this inlet-entrance area are related to the size and shape of the unlocking instrument, FIGS. 7, 8, of this invention. The unlocking instruments will be described in the description of FIGS. 7, 8. The position of the integrated ligature, when unlocked from the ligature receiving channel, can be seen in the broken line of FIG. 1(66). The unlocked position of the ligature is shown by the broken lines defining its shape and position.

The small raised area, FIG. 1(44). at the upper side margin of the bracket, facing the examiner, is a barrier-stop. The barrier-stop restrains the ligature from unlocking, if unanticipated forces are placed upon the ligature, when it is in a closed and locked position. The shape memory incorporated in the ligature wire, causes the ligature wire to resist any forces placed upon it to change its shape, and thereby is a deterrent to any unlocking forces.

FIG. 1(66), is a broken line illustration of the position to which the integrated ligature, FIG. 1(20, 20-b), has moved during the unlocking procedure. This movement frees the ligature from confinement in the channel at the upper side of the bracket. This broken line illustration also shows the change in the position, and relationship of the ligature to the defining shapes, of the various areas of the bracket, that the ligature progresses along, and those areas that it becomes integrated thereto. These changes in the position of the integrated ligature, are allowed by the unobvious temporary flexing of the straight-beam shaped portion of the integrated ligature, FIG. 2(20b) that resides in the ligature receiving channel at the lower side of the bracket, FIG. 2(24). This straight-beam shaped portion responds to the forces exerted by the unlocking instrument, FIG. 7,,8, used at the upper side of the bracket, which faces the examiner of FIG. 1. The relationship of the straight-beam shaped portion of the ligature,, to the curved wall of the ligature receiving channel at the lower side of the bracket, FIG. 2(46), is an important ingredient, that allows the ligature to move. The resultant movement along the mesial and distal sides of the bracket, and at the upper side of the bracket, allow for the integrated ligature to become unlocked and free from the upper side of the bracket, FIG. 1(66-b).

FIG. 2, is an illustration of the Integrated Ligature and Orthodontic Bracket, with the lower side facing downward. The illustration depicts the version of the bracket having one arch wire receiving channel in the bracket, called the horizontal channel. It can be seen that the ligature receiving channel, FIG. 2(24), at the lower side of the bracket, has a different configuration than the upper side viewed in FIG. 1(24). Of particular importance in FIG. 2 is the see-through curved broken line, FIG. 2(46), showing the contour of the wall at the base of this ligature receiving channel. The contour of this curved wall is again shown from a different perspective in FIG. 6(46). You can also see the flanged area, FIG. 2(32),, and observe the see-through broken line of portions of the integrated ligature wire, FIG. 2(20-b). The ligature wire is poised away from the curved side of the base of the channel, FIG. 2(46), except at the small are of contact, at the most convex area of this curved wall of the channel, FIG. 2(48). The portion of the ligature, that is poised, in relation to the curved side of the channel, is shaped like a straight bean, FIG. 2(20-b). This straight beam shaped portion of the ligature, will temporarily flex toward the curved convex shaped wall of the base of this channel. This flexing occurs when the ligature is unlocked, at the opposite end, of the bracket. The curved convex shape of the floor of the ligature receiving channel, FIG. 2(46)

provides the space for the straight beam shaped portion of the ligature, to move into, as the beam flexes temporarily. When the beam flexes,, the end areas of the beam move toward the curved base side of the channel.

Figure 4:
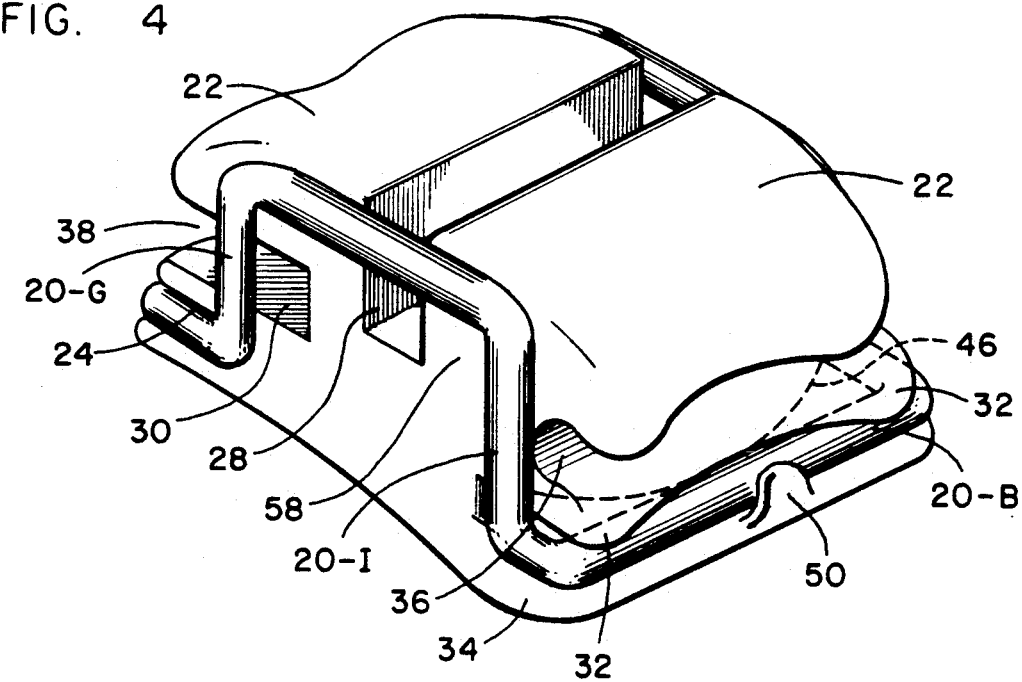
FIG. 4, is and illustration of the Integrated Ligature and Bracket with the lower side facing downwards. The illustration portrays the version of the bracket having two arch wire receiving channels. The two channels are a horizontal channel and vertical channel.
Figure 5:
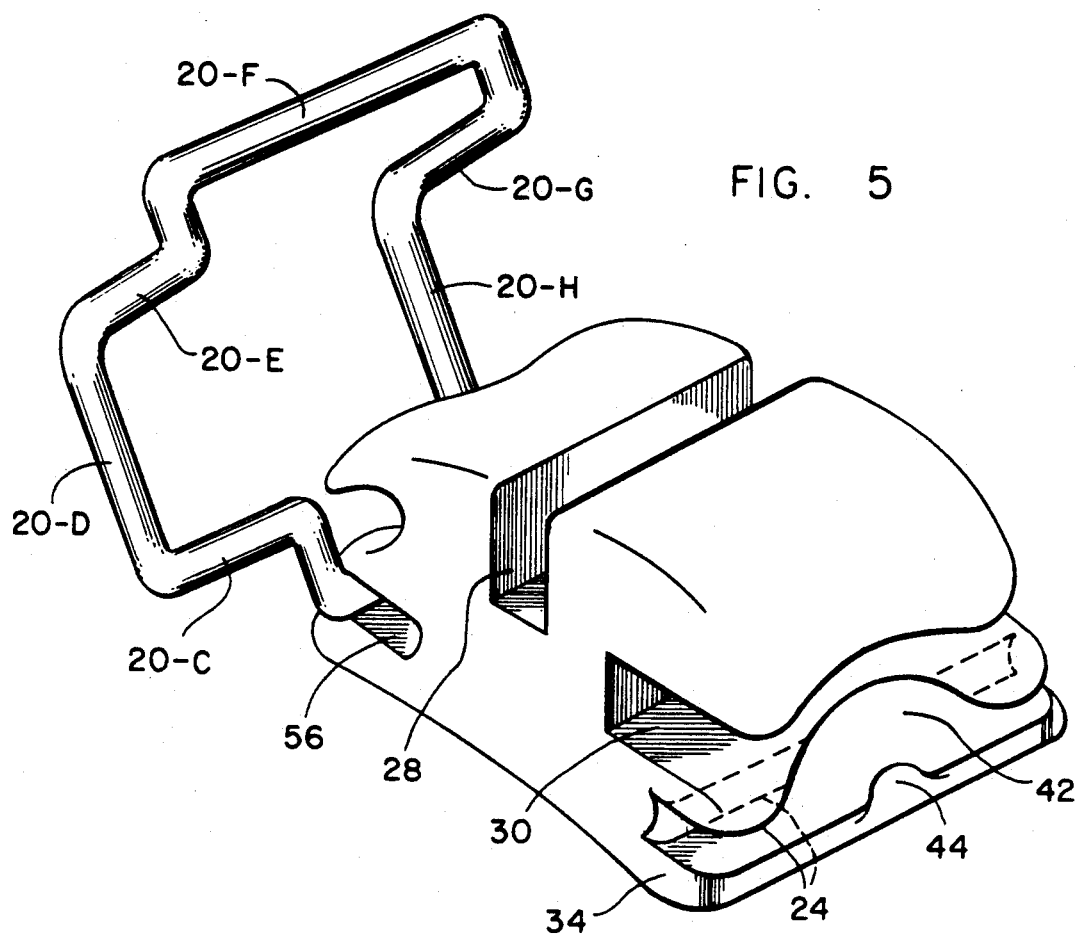
FIG. 5, is an illustration of the Integrated Ligature and Bracket, with the upper side of the brackets facing the examiner thereof. The illustration portrays the ligature in a fully open position, and the two arch wire receiving channels fully free of the ligature.

This temporary flexing of the straight-beam shaped portion of the ligature, FIG. 2(20-b), allows the portions of the ligature, along the mesial and distal sides of the bracket, FIG. 5 (20-c, d, e, g, h) and FIG. 4(20-I), to move toward the unlocking area at the opposite end of the bracket. Therefore, there is a specific relationship to the distance, that the ends of the straight-beam shaped portion of the ligature travel, when it flexes temporarily, and the amount the ligature travels at the opposite end of the bracket. This travel frees the ligature from the ligature receiving channel and frees the ligature from its locked position. The ends of the beam shaped area travel the distance necessary to free the integrated ligature from its locked position.

At the conclusion of the unlocking procedure, the straight beam portion of the ligature, returns from its flexed position to its straight beam shaped position. The force to cause the straight beam shaped portion to temporarily flex is caused by the rotation of the unlocking instrument at the inlet-entrance, FIG. 1(42) at the upper end of the bracket. The widest side of the unlocking instrument is equal to the distance of movement of the ligature that is necessary to unlock it from the bracket.

Figure 9:
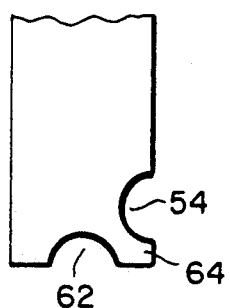
FIG. 9, is an illustration of the end portion of the instrument used to unlock or lock the Integrated Ligature at the lower side of the Bracket. This instrument is also used to place the ligature into a locked position at the upper side of the bracket. The illustration is a view of the widest side of the instrument.
Figure 10:
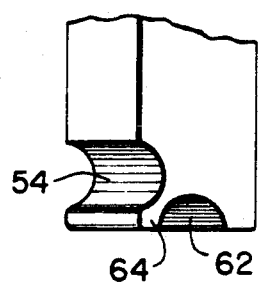
FIG. 10, is an illustration of an oblique view of the instrument illustration in FIG. 9. This view illustrates the difference in the width to the thickness of the instrument.

The ligature at the lower side of the bracket, FIG. 2, has a different locking arangement, than is shown at the upper side of the bracket in FIG. 1. The ligature within the lower side of the bracket, FIG. 2(20-b), can be unlocked, and the ligature can be completely removed from the bracket. The unlocking instrument, FIGS. 9, 10, is used in unlocking the ligature from the lower side of the bracket. The ligature is most easily completely removed from the bracket when the ligature is fully free, open, and away form all other channels of the bracket, FIG. 5. It is not intended that the ligature would be routinely unlocked and removed from the lower side of the bracket. It can be unlocked and removed and then replaced and locked into the channel, if treatment circumstances dictate that it should be done. Therefore, the entire ligature can be removed from the bracket, if desired. The ligature having been removed, can be re-placed, or a new, and differently shaped ligature can be placed. The difference in shape would be along the proximity of the ligature to the mesial and distal sides of the bracket. The portion of the ligature that is received into the ligature receiving area at the upper and lower ends of the bracket, are constant in size, and are not different in one ligature as compared to another ligature.

FIG. 3, is an illustration of the Integrated Ligature and Bracket, with the upper side facing the examiner. The illustration depicts the version of the bracket having two arch wire receiving channels. These two channels are, a horizontal channel and a vertical channel. The bracket has a retention cove area, FIG. 3(38), that is formed at the upper end of the bracket, by the parked position of the closed ligature in relation to the vertical channel, FIG. 3(20-e). The portion of the ligature that integrates with the mesial and distal sides of the bracket, has a shape defining its relation to two arch wire receiving channels. There are two arch wire receiving channels in the bracket, FIG. 3(28, 30). The first channel traverses the facial side of the bracket in a mesial to distal direction. This channel is called the horizontal channel, FIG. 3(28). The second arch wire receiving channel is in the upper side of the bracket FIG. 3(30). This second channel is called the vertical channel. The vertical channel traverses the bracket in a mesial to distal direction within the upper side of the bracket. The open side of the channel faces upward. The vertical channel is divided by the integrated ligature, when the ligature is in a closed position. FIG. 3(20-E). This closed position causes the ligature to divide the vertical channel into two portions. The deepest portion of the vertical channel is an arch wire receiving channel. The second portion of the vertical channel has now become the retention cove area at the upper side of the bracket. The two arch wire receiving channels in this bracket are a horizontal channel and a vertical channel. When the integrated ligature is in a locked position, the orthodontic arch wire in the vertical channel would be confined therein by the ligature. The retention cove area FIG. 3(38) is used to retain auxiliary devices and/or supplemental ligatures used in orthodontic treatment. The integrated ligature and bracket of FIG. 3 can accommodate an orthodontic arch wire in either arch wire receiving channel, or in both arch wire receiving channels simultaneously.

The locking and unlocking methods are unchanged by the presence of the vertical channel and horizontal channel.

FIG. 4, is an illustration of the Integrated Ligature and Bracket with the lower side facing downward. The illustration portrays the version of the bracket having two arch wire receiving channels. These two channels are, a horizontal channel and a vertical channel. The retention cove area is present at the lower and upper ends of the bracket. The lower side of the bracket, FIG. 4 has a ligature receiving channel like-to that in FIG. 2, and it functions in the same manner as presented in the description of FIG. 2. The progression of the integrated ligature, as it related to the defining formed mesial and distal sides of the bracket, has a configuration, to allow the ligature to travel toward the upper side of the bracket during the unlocking or locking procedure at the upper end of the bracket. This defining form of the ligature prevents imprignment of the ligature upon the horizontal channel FIG. 4(28), when the portion of the ligature, FIG. 4(20-I), moves toward the vacant area FIG. 4(58) during the unlocking and locking procedures of the ligature.

This ability to travel results from the temporary flexing of the straight beam-shaped portion of the ligature, FIG. 4(20-b). This travel results from and is demanded by the forces exerted by the unlocking instrument at the upper side of the bracket.

FIG. 5, is an illustration of the Integrated Ligature and Bracket, with the upper side of the bracket facing the examiner. The illustration portrays the ligature in a fully open position, and the two arch wire receiving channels fully free of the ligature. FIG. 5(20-c thru 20-H). This open position of the ligature shows the accessibility of the two arch wire receiving channels, FIG. 5(28, 30), and the defining formed shape of the bracket, and the defining formed shape of the ligature, FIG. 5(20-c), through 20-H and FIG. 1(20-b) and FIG. 4-(20-I).

The ligature receiving channel, FIG. 5(24), can be seen without the ligature present therein. The ligature receiving channel, FIG. 5(24), can be seen traversing the upper end of the bracket in a mesial to distal direction. This channel has its open side facing toward the upper end of the bracket. The walls of the channel form walls of a rectangle as it traverses in a mesial to distal direction in the upper side of the bracket. The walls are constant in their planes, and the facial wall is partially interupted in its middle position to provide an inlet entrance for the unlocking instrument, FIG. 5(42). This inlet shaped area is of a size to accommodate the ligature unlocking instrument, and the forces generated by the rotation of the unlocking instrument.

The vertical channel (FIG. 5(30), at the upper end of the bracket has its open side facing the upper side of the bracket. This arch wire receiving channel progresses in a mesial to distal direction in its defining formed shape. The walls of the vertical channel form walls of a rectangle in relation to each other as the walls progress, in a mesial to distal direction within the upper side of the bracket. The walls of the vertical channel also form the two walls of the retention cove area that face each other. The third wall of the retention cove area is formed by, the position and parking, of a portion of the integrated ligature. This portion of the ligature bisects the vertical channel when the ligature is in a closed position.

The ligature of the invention has portions of its formed shape, that have a specific relationship to specific areas of the formed shape of the bracket. There are each of two portions of the ligature that have a specific relationship to each of the two ligature receiving areas of the bracket, (FIG. 1(20-b) and FIG. 2(20-f). There are each of two portions that have a specific relationship to the arch wire receiving channels of the bracket, FIG. 5(20-d, 20-h). There are each of two portions of the ligature that have a specific relation to the vertical arch wire receiving channel of the bracket, and to the forming of a side of the retention cove area, (FIG. 3(20-E), and FIG. 5(20-g). The ligature, therefore, has a defining formed shape to participate in integration with the bracket, and to participate in the locking and unlocking mechanical procedure, and to participate in the formation of the base of the retention cove area, by bisecting the vertical channel of the bracket.

Figure 6:
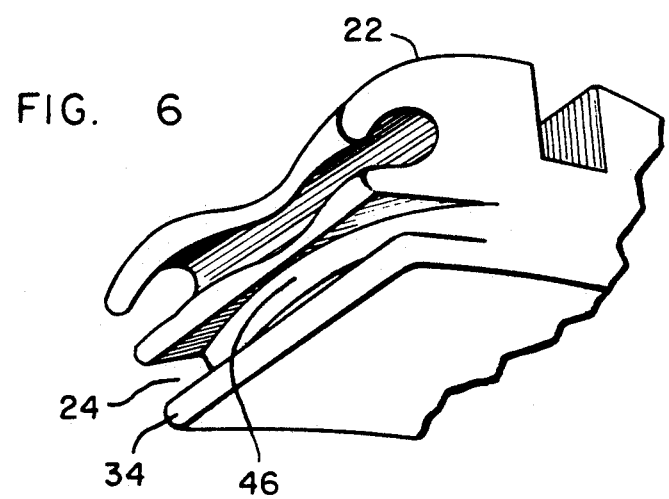
FIG. 6, is an illustration of the lower side of the bracket, elevated to a plane, to depict the ligature receiving channel and the curved convex shape of the base of that channel.

FIG. 6, is an illustration of the lower end of the bracket elevated to a plane, to depict the ligature receiving channel, FIG. 6(24), and the curved-convex wall at the base of the channel, FIG. 6(46). When viewed from the lower side of the bracket, the ligature receiving channel has a convex shape of the wall at the base of channel as the wall progresses from the mesial side to the distal side, of the bracket. FIG. 6(46).

The ligature receiving channel at the lower side of the bracket, FIG. 6(24) if formed of walls which provide a cross-section which is rectangular, and having one wall progressing along a curvature, as it is joined at right angles to the channel walls that face each other. The curvature of the curved wall, FIG. 2(46), FIG. 6(46), is scribed by a constant radius of a portion of a circle. The curvature of this wall is convex when viewed from the open side of the channel. The ligature wire in its integrated relation to this ligature receiving channel, is shaped like-to a straight-beam. FIG. 2(20-b). The ligature is poised away from the convex surface, except in a small middle-area of the convex surface of the ligature receiving channel, FIG. 2(48).

FIG. 7, is an illustration of the end portion of the instrument, used to unlock the Integrated Ligature from the upper side of the Bracket. This illustration is a view of the widest side of the instrument. The instrument is approximately twice as wide as it is thick. The notch in the side of the instrument, FIG. 7(54), is slightly larger than the diameter of the portion of the integrated ligature that is present in the locking and unlocking area. The depth to which this semicircular notch, FIG. 7(54) progresses into the surface of the instrument should not imping on the distance of the remaining width of the instrument that must be present to unlock the ligature, when the instrument is rotated in the inlet entrance of the bracket. During the unlocking procedure the instrument is rotated. The two-to-one ratio of the width to thickness of the instrument, when rotated, causes a change in the position of the ligature. This change causes the ligature to become free from the channel in which it had been residing.

The end of the unlocking instrument is convex, FIG. 7(56), in shape. This provides for a favorable tipping of the instrument to provide some flexibility of the positional use and utility of the instrument.

FIG. 8, is an illustration of an oblique view of the instrument shown in FIG. 7. The thickness of the instrument FIG. 8(58) compared to width FIG. 8(60) can be seen in this oblique view.

FIG. 9, is an illustration of the end portion of the instrument used to unlock or lock the Integrated Ligature at the lower side of the bracket. This instrument is also used to replace the Ligature into a locked position at the upper side of the Bracket. This illustration FIG. 9 is a view of the widest side of the instrument.

The instrument of FIG. 9 has two semicircular notches in each of two surfaces of the instrument, FIG. 9(54, 62). These two notches are similar in size and shape, to be useful in relating to the size and shape of the ligature. The size of each of the two notches is to be slightly larger than the diameter of the ligature. This slightly larger size provides for greater utility of the instrument, by providing a non-binding and reduced frictional relation to ligature, in the unlocking and locking procedures. The position of the two notches in relation to each other, FIG. 9(54, 62), form a peninsular shaped area, FIG. 9(64) the isthmus of which is formed by the sides of the adjacent notches.

FIG. 10, is an illustration of an oblique view of the end portion of the instrument illustrated in FIG. 9. FIG. 10 shows a semicircular notch in the narrow side of the instrument FIG. 10(54) and a semicircular notch in the adjacent end-side of the instrument FIG. 10(62). These two semicircular notches form a peninsular shape and isthmus that connects with the body of the instrument. The width and thickness of this instrument is the same as the instruments of FIG. 7 and FIG. 8.

Figure 11:
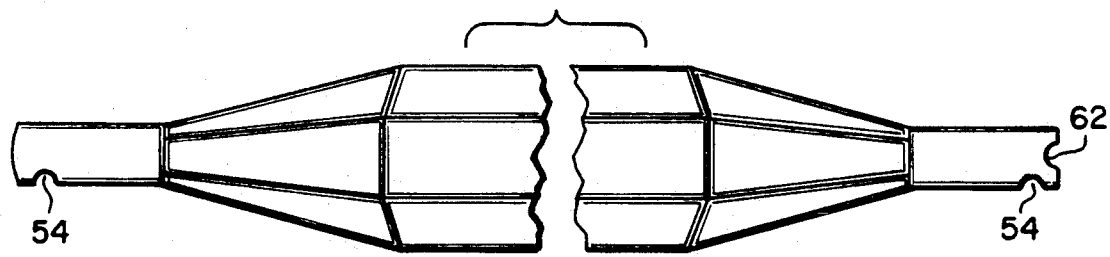
FIG. 11, is an illustration of a version of the handle portion of the instruments shown in FIGS. 7,8 and FIGS. 9,10. The illustration shows the presence at each end of the handle, of one of each of the two instruments shown in FIGS. 7.8 and FIGS. 9,10.

FIG. 11, is an illustration of a view of an embodiment of the instrument that would have end portions like-to the instruments depicted in FIG. 7 and 8 and FIG. 9 and 10. FIG. 11 is an illustration of one of the potential shapes of the handle portion of the instruments illustrated in FIGS. 7, 8 and FIGS. 9, 10.

The illustrations in FIGS. 7, 8 , 9 and 10 illustrate the defining formed shapes of the instruments that will be actively engaged in the locking and unlocking procedures of the integrated ligature, at the upper end and/or lower end of the integrated ligature and bracket. FIG. 11 is a portion of a straight handle for each or both of the instruments illustrated in FIGS. 7,8 and FIGS. 9,10.

The handle is an elongated body of metal, on other suitable material. The sides of the handle can be circular in form, or a form defining a plane figure having six angles and six sides of a hexagon, or any combination of forms that define a handle shaped to be used by h hands, and facilitates the use of the instrument. The instrument illustrated in FIG. 7 and FIG. 8 can be placed at one end of the handle, and the instrument illustrated in FIG. 9 and FIG. 10 can be placed at the other end of the handle, to provide an efficient availability for the use of each of both instrument.

Figure 12:
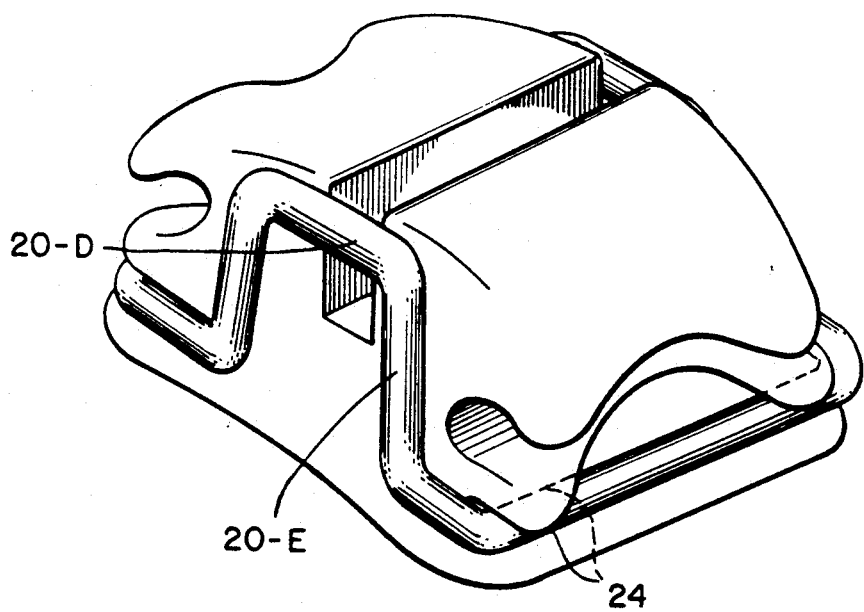
FIG. 12, is an illustration of the Integrated Ligature and Orthodontic Bracket, with the upper side facing the examiner thereof. The integrated ligature and bracket is similar to the integrated ligature and bracket of FIG. 1, except for two differences.

FIG. 12, is an illustration of the Integrated Ligature and Orthodontic bracket, with the upper side of the bracket facing the examiner thereof. This integrated ligature and bracket is similar to the integrated ligature and bracket of FIG. 1, except for two difference. The barrier-stop is not present, and the ligature receiving channel has more depth as it traverses the upper side of the bracket in a mesial to distal direction.

The increased depth of the ligature receiving channel FIG. 12 (24) provides for additional mechanical retention of the ligature within the channel. This added mechanism retention is augmented by the shape memory properties of the metal of which the ligature is made. This bracket does not have a vertical arch wire receiving channel present in its formed shape. Therefore, the forces, that might prevail to dislodge the ligature from the channel, are not present. The mechanical relation of the ligature to the bracket, and the insistence of the shape memory ligature to resist distortion if its shape, are factors that allow this bracket to function in an integrated manner with the ligature, without a barrier-stop at the upper side of the bracket.

The defining shape of the integrated ligature is changed slightly, to accommodate the increased depth of the ligature receiving channel, and for the ligature to assume a fully integrated position in the ligature receiving channel.

The small change of the defining shape of the ligature, is a decrease in the angle formed by the juncture of the two portions of the ligature that approximate the horizontal channel of the bracket, and then progresses in its formed shape to enter the ligature receiving channel, FIG. 12 (20-D and 20-E). Two portions of the ligature approximate the opposite side of the bracket in a similar manner and at a similar angle of relationship. FIG. 5,(20-G and 20-H).

The use and operation of the invention becomes more apparent when the following are considered.

The ligature FIG. 1,2,3,4,5,12 is made of metal that has a shape memory, and therefore always makes an effort to return to its original shape, when it is temporarily forcibly distorted. Other metals may be used if they meet the requirements of the necessary physical properties, particularly those that maintain form and do not fatigue during multiple times of usage.

The ligature has a new, unique, novel, and unobvious relation to the convex curved surface of the ligature receiving channel at the lower side of the bracket.

The ligature is easily unlocked and locked in its relation to the bracket.

The ligature can be completely removed from the bracket, if necessary, and replaced easily.

A different ligature, having a different relation to the arch wire receiving channel or channels can be placed. However, the relationship of the ligature to the ligature receiving channels is always the same.

The ligature contributes to the comfort of its presence. because of its resilient response to forces placed upon it.

The roundness of the ligature enhances the rounded contour of the Integrated Ligature and Bracket.

The flexibility of the ligature and the shape memory properties of the ligature, facilitate the locking and unlocking convenience of the ligature.

The special shape memory feature of the ligature provides an insistence, on its behalf, to remain in the locked position, until the instrument is used to unlock it.

The ligature has physical values and shape memory values to avoid any harshness of its physical responses and thereby is comfortable, efficient and predictable when utilized.

The ligature is integrated with the bracket, in its defining formed shape, to have a relevancy to the channels, surfaces, and functional uses, of the bracket.

The integrated ligature has various portions of the ligature that relate to specific areas of the brackets.

The shape of the integrated ligature is defined in the drawings where numerical references are used as follows: In FIG. 1, FIG. 4(20-I), (20-b), in FIG. 5 (20-c, 20-d, 20-E,20-F, 20-g, 20-H.)

The portion of the ligature that is received into the ligature receiving channel of the upper and lower sides of the bracket have a particular shape. FIG. 1(20-b) and FIG. 5(20-F).

The portion of the ligature that relates to the horizontal channel has a defining shape to accomplish that relationship. FIG. 5(20-d,20-h).

The portion of the ligature that participates in the formation of the base of the retention cove, has a defining shape that is particularly relevant, when the bracket has a vertical channel therein. FIG. 5(20-E and 20-G).

The portion of the ligature that travels along the mesial and distal sides of the bracket during the locking and unlocking procedures, has a defining shape to prevent encroachment of the traveling ligature upon the internal channel dimensions of the horizontal channel of the bracket. FIG. 4(20-I) and FIG. 5(20-C).

The bracket has small size while incorporating the most desirable features of the two primary types of brackets and the two primary types of ligature revealed in the prior art.

The bracket has an uncomplicated defining formed shape that makes it functional in a very small device.

The bracket by its unique convex surface, within the ligature receiving channel in the lower side of the bracket, provides a new, novel and unobvious surprising functional feature to the integration of the ligature and the bracket.

The ligature receiving channel at the upper side of the bracket has an interior rectangular shape in the areas that relate to the ligature, and thereby have a dependable fitting relation to the ligature.

The ligature receiving channel at the lower side of the bracket has two interior surfaces of the channel that face each other at right angles; when viewing the formed channel from the lower end of the bracket, the base of the channel is seen to be convex in shape. The convex, curved shape wall is joined by the two sides facing each other at right angles, to form the sides of this rectangular shaped ligature receiving channel.

The ligature receiving channels at the upper and lower sides of the bracket have shapes along their margins, at the open side of the channel to facilitate the retention of the integrated ligature after it is placed in the channel. These shapes along the margins at the open side of the channel also facilitate the placement of the ligature in the confining area of the ligature receiving channel, and within proximity to the barrier-stop, that is present in the margin area of the bracket. The barrier stop is located at the middle of the margin area, that joins the margin of the base of the bracket. The placement of and removal of the ligature at the upper side and lower side of the brackets, requires the ligature to be flexed temporarily to follow the shape of the margin of the open side of the channel that faces the upper side or the lower side of the bracket respectively. The curvature of the margin of the flange area is convex, and the margin of the mid-area of the bracket is concave. The ligature is flexed, using the instrument described in FIGS. 7,8 or FIGS. 9,10 to whipe and/or rotated the ligature into its locked position, or to remove the ligature from its locked position. It immediately acquires a retentive stance in relation to the ligature receiving channel. The ligature enters the channel by flexing to enter the space bounded by, the convex margin of the two flanges, and the concave margin of the middle area of the channel that resides between the two flanges. The barrier-stop provides a confinement boundary for the ligature, opposite the concave area, at a distance sufficient for the ligature to reside passively in the ligature receiving channel.

The ligature receiving channels and the arch wire receiving channels, have sides that form rectangles in their relationship.

The invention described in the embodiment of the invention provides, new, useful, novel, and unexpected ingredients of the Integrated Ligature and Orthodontic Bracket of the invention.

The invention provides a unique synthesis of advantages of the two primary types of ligatures and the two primary types of brackets. The embodiment of the invention provides discovery of the initially unobvious features and functions, and bring them into an obvious synthesis of newness and usefulness.

It should be understood, that the foregoing disclosure and specifications relate to particular and preferred embodiments of the invention, and that the foregoing disclosure is intended to cover all changes and modifications of the examples of the invention herein chosen for purposes of disclosure, which do not constitute departures from the spirit and scope of the invention.

What is claimed is:

1. An orthodontic appliance for use with orthodontic auxiliary devices including arch wires, tie rings and the like so as to apply corrective forces to teeth, said appliance comprising:

an orthodontic bracket having an inner surface that is engageable with a surface on a tooth and an outer side facing away from the inner surface in either a facial or a lingual direction depending upon the surface of the tooth engaged by the inner surface, said bracket also having a mesial side and a distal side and an upper side and a lower side joining the mesial and distal sides, said bracket having a receiving channel formed therein for receiving and holding an auxiliary device, and a ligature combined with the bracket for confining an auxiliary device positioned in said receiving channel, said ligature being an endless wire formed to a generally loop shape and having spaced-apart first and second legs joined by spaced-apart side members, the side members cooperating with the receiving channel to prevent an auxiliary device received in the channel from being removed while the ligature is in place on the bracket, said bracket having a first ligature receiving means in said upper side for receiving the first leg of the ligature and a second ligature receiving means in said lower side of the bracket for receiving the second leg of the ligature, said second ligature receiving means in said lower side of said formed bracket having a curved portion that is convex in curvature when said ligature receiving means is viewed from the lower side of said bracket, said ligature being constructed of a material having shape-memory so that the ligature can be installed on the bracket by inserting the second leg in the second ligature receiving means and bending the ligature within its elastic limit until the first leg is positioned in the first ligature receiving means and allowing the ligature to return to its original shape wherein it is retained on the bracket.

2. The orthodontic appliance of claim 1 in which the auxiliary device receiving channel has an open side facing the outer side of said bracket, and the side members of the ligature extend over an auxiliary device positioned in the channel to confine the device in the channel.

3. The orthodontic appliance of claim 2 in which the first and second ligature receiving means are recesses formed in and open from the upper and lower sides of the bracket, and the recesses have margins that traverse the bracket in a mesial to distal direction.

4. The orthodontic appliance of claim 3 in which the recesses of the first and second ligature receiving means each have walls that extend substantially longitudinally through the bracket in a mesial to distal direction;

5. The orthodontic appliance of claim 4 in which the recesses of the first and second ligature receiving means each have an open side of a size that provides access for the respective leg of the ligature.

6. The orthodontic appliance of claim 3 in which a detent is formed on the bracket adjacent to the recess of the first ligature receiving means, the detent being positioned a sufficient distance from the margins of the recess to provide for entry into the recess5 of the first leg of the ligature and to retain the ligature in place on the bracket when the first leg is positioned in the recess.

7. The orthodontic appliance of claim 6 in which the margins along the entry to the recess have a contour progressing in a mesial to distal direction that in progression forms a convex-to-concave-to-convex formed margin.

8. The orthodontic appliance of claim 7 in which the concave portion of said margins defines a space providing for entry of an unlocking tool to engage the leg of the ligature positioned in the recess and force the leg over the detent.

9. The orthodontic appliance of claim 6 in which a detent is also formed on the bracket adjacent to the recess of the second ligature receiving means, the detent being positioned a sufficient distance from the margins of the recess to provide for entry into the recess of the second leg of the ligature and to retain the ligature in place on the bracket when the second leg is positioned in the recess.

10. The orthodontic appliance of claim 2 in which the receiving channel extends through the outer side of the bracket in a mesial-distal direction between the upper and lower sides with its open side facing the outer facial-lingual side of the bracket.

11. The orthodontic appliance of claim 10 in which said bracket has a second auxiliary device receiving channel formed in the outer side of the bracket, said second receiving channel extending in a mesial-distal direction near the upper side with its open side facing the upper side of the bracket.

12. The orthodontic appliance of claim 11 in which the spaced apart side members of the ligature bisect the second auxiliary device receiving channel in a facial-lingual direction.

13. The orthodontic appliance of claim 12 in which the spaced apart side members of the ligature by bisecting the second auxiliary receiving channel thereby define the boundaries of movement of any auxiliary device positioned in the said receiving channel.

14. The orthodontic appliance of claim 1 in which the bracket also has an auxiliary device retention groove formed in the lower side of the bracket.

15. The orthodontic appliance of claim 14 in which the bracket also has an auxiliary device retention groove formed in the upper side of the bracket.

16. The orthodontic appliance of claim 1 in which the first and second legs of the ligature are substantially straight when positioned passively in their respective ligature receiving means.

17. The orthodontic appliance of claim 16 in which the straight second leg is engaged against the convex shaped portion of the second ligature receiving means in said lower side of said bracket when seated in said second ligature receiving means.

18. The orthodontic appliance of claim 17 in which the straight second leg of the ligature is in contact with said convex shaped portion only at the middle area of said convex shaped portion.

19. The orthodontic appliance of claim 18 in which said straight second leg will flex toward said convex shaped portion in response to force applied to the first leg of the ligature.

* * * * *